(12) United States Patent
Kritzler et al.

(10) Patent No.: US 10,070,644 B2
(45) Date of Patent: Sep. 11, 2018

(54) ANTIMICROBIAL COMPOSITION

(71) Applicant: Novapharm Research (Australia) Pty Ltd, Rosebery (AU)

(72) Inventors: Steven Kritzler, Cronulla (AU); Hyo Sang Kwon, Rosebery (AU)

(73) Assignee: Novapharm Research (Australlia) Pty Ltd (AU)

( * ) Notice: Subject to any disclaimer, the term of this patent is extended or adjusted under 35 U.S.C. 154(b) by 0 days.

(21) Appl. No.: 14/654,865

(22) PCT Filed: Dec. 19, 2013

(86) PCT No.: PCT/AU2013/001489
§ 371 (c)(1),
(2) Date: Jun. 23, 2015

(87) PCT Pub. No.: WO2014/100851
PCT Pub. Date: Jul. 3, 2014

(65) Prior Publication Data
US 2015/0342181 A1 Dec. 3, 2015

(30) Foreign Application Priority Data
Dec. 24, 2012 (AU) .................................. 2012905697

(51) Int. Cl.
| | | |
|---|---|---|
| A01N 25/04 | (2006.01) | |
| A01N 47/44 | (2006.01) | |
| A01N 31/16 | (2006.01) | |
| A01N 31/02 | (2006.01) | |
| A01N 31/14 | (2006.01) | |
| A61K 31/085 | (2006.01) | |
| A61K 31/155 | (2006.01) | |
| A61K 31/23 | (2006.01) | |

(52) U.S. Cl.
CPC .............. *A01N 25/04* (2013.01); *A01N 31/02* (2013.01); *A01N 31/14* (2013.01); *A01N 31/16* (2013.01); *A01N 47/44* (2013.01); *A61K 31/085* (2013.01); *A61K 31/155* (2013.01); *A61K 31/23* (2013.01)

(58) Field of Classification Search
None
See application file for complete search history.

(56) References Cited

U.S. PATENT DOCUMENTS

| | | | |
|---|---|---|---|
| 6,617,294 B2 | 9/2003 | Narula et al. | |
| 9,089,129 B2 | 7/2015 | Heisig et al. | |
| 2001/0033854 A1* | 10/2001 | Johnson | A61K 8/046 424/405 |
| 2003/0139307 A1 | 7/2003 | Narula et al. | |
| 2004/0146479 A1 | 7/2004 | Kritzler | |
| 2004/0166070 A1 | 8/2004 | Galdi et al. | |
| 2006/0193745 A1 | 8/2006 | Arndt et al. | |
| 2011/0117048 A1* | 5/2011 | Kritzler | A01N 25/02 424/78.07 |
| 2013/0338236 A1* | 12/2013 | Agarwal | A61K 47/12 514/724 |

FOREIGN PATENT DOCUMENTS

| | | | | |
|---|---|---|---|---|
| EP | 1683416 A1 * | 7/2006 | | A01N 43/40 |
| JP | 2011032273 A | 2/2011 | | |
| WO | 03/006071 A1 | 1/2003 | | |
| WO | 2007061028 A1 | 5/2007 | | |
| WO | 2007140442 A2 | 12/2007 | | |
| WO | 2010147868 A2 | 12/2010 | | |
| WO | 2013/192034 A2 | 12/2013 | | |

OTHER PUBLICATIONS

European Search Report for European Patent Application No. 13867548.3 corresponding to PCT/AU2013/001489, dated Jun. 16, 2016 (10 pages).
European Standard EN 1500, Jul. 1, 1997 (22 pages).
"Dipropylene glycol (DPG) Product Stewardship Summary," Oct. 1, 2011 (2 pages).
International Search Report for PCT/AU2013/001489, dated Mar. 12, 2014 (4 pages).
International Preliminary Report on Patentability for PCT/AU2013/001489, with Amended Pages, dated Apr. 7, 2015 (13 pages).
Garruto et al., "Advice to the Lab Lorn—Jun. 2003—Free Radical Technology," [retrieved on Feb. 28, 2014]. Retrieved from Internet <URL: http://radicaltechnology.com/articles/advice-jun2003.pdf> published on Oct. 18, 2012 as per Wayback Machine.
Fraise et al, "Principles and Practice of Disinfection, Preservation & Sterilization," Blackwell Publishing Ltd (2004) 4th edition, ISBN 1-4051-0199-7, pp. 545-546.
Office Action in Japanese Patent Application No. 2015-548111 dated Jun. 20, 2017 (6 pages).
English translation for Office Action of Japanese Patent Application No. 2015-548111 dated Jun. 20, 2017 (9 pages).
Machine translation of WO 2007/061028 (21 pages).
Machine translation of JP 2011-032273 A (30 pages).

* cited by examiner

*Primary Examiner* — Susan T Tran
*Assistant Examiner* — William A Craigo
(74) *Attorney, Agent, or Firm* — Thrive IP®; Jeremy M. Stipkala

(57) ABSTRACT

Antiseptic hand rub composition comprising at least 0.2% w/w of isopropyl myristate, free from other derivatives of myristic acid. Phenoxyethanol is preferably present in the composition at a concentration of 1% by wt or less. A glycol may also be present, such as dipropylene glycol if the composition is an ethanol based hand rub gel or propylene glycol if the composition is in the form of an emulsion or dispersion. Additional biocides such as triclosan and chlorhexidine gluconate may be included.

8 Claims, No Drawings

ANTIMICROBIAL COMPOSITION

RELATED APPLICATIONS

This application represents the U.S. National Phase under 35 U.S.C. § 371 of International Patent Application No. PCT/AU2013/001489, filed Dec. 19, 2013, entitled, "IMPROVED ANTIMICROBIAL COMPOSITION," and claims benefit of priority to Australian Patent Application No. 2012905697, also entitled, "IMPROVED ANTIMICROBIAL COMPOSITION," filed on Dec. 24, 2012, the disclosure of which international application and Australian application are incorporated herein by reference in their entirety.

BACKGROUND

The use of alcohol as an antimicrobial dates to biblical times and earlier. Alcohol-containing antimicrobial compositions have been widely used in hospitals since at least the 1990's. In 1993, Bruch et al (U.S. Pat. No. 5,403,864) stated:—

"Infection control and epidemiology experts have repeatedly emphasized that the single most important element in reducing the spread of infection is hand washing because a common method of transfer among individuals in the health care environment is with the hands. This fact has been painfully demonstrated in the analysis of epidemic spread. However obvious and simple this may seem, medical care personnel, including physicians and nurses, are reluctant to wash or scrub their hands as frequently as required by their own protocols. It is estimated that the average time of washing between patients is 10 sec or less. The effectiveness of soap-and-water washing is measured in terms of minutes. Most simply do not wash frequently enough . . . .

When a health care worker handles equipment or patients, bacteria which are not a part of the normal skin flora are picked up and adhere loosely to the topmost skin layer, the stratum corneum."

These statements remain as true in 2012 as when written in 1993. However in the intervening 20 years, new and improved antimicrobial preparations have been developed and the significance of two additional facts has become apparent. Firstly, some microorganisms may reside more deeply in sub corneum strata. Secondly, the major reason for non-compliance with protocols is drying and chapping of the hands and skin irritation caused by repeated use of alcoholic rubs or water based antiseptic washes. Attempts to minimize irritation by inclusion of emollients have not been effective at increasing compliance either (i) because the emollients contributed to a feeling of greasiness after use or (ii) because they reduced the speed with which the hand wash was effective, or (iii) at the concentrations required, the emollients were ineffective at skin irritation reduction or for a combination of these three reasons.

In 1995 Bruch et al disclosed an antimicrobial composition comprising Triclosan, chloroxyphenol and an alcohol but this composition was not effective against subcutaneous organisms and although the inventors claimed that no signs of irritation were exhibited after multiple uses in the laboratory, many cases of skin irritation were exhibited in hospital use.

In 1998 Jampani et al (U.S. Pat. No. 6,022,551) noted a need for an antimicrobial composition that is effective while also being non-irritating to users, and described a composition containing specific thickeners, and phospholipids The present Inventors have found that subjective feel of the composition also plays an important role in compliance, irrespective of other factors, and it is not sufficient for a composition to be "non-irritating". Thus, staff who may have to apply compositions to their hands as frequently as 100 times a day if they are to fully comply with protocols have been found to have a much higher compliance rate if using preparations which they judge to feel good, than if using preparations which they do not judge to feel good, or which they judge to feel inferior to other preparations they have used which they judge to feel better. One of the factors influencing feel is the tendency to pill exhibited by some alcoholic gel preparations, but other factors include greasiness, and other subjective factors which play a major role in affecting how the composition feels when used and hence compliance rates. Preparations which are generally judged by staff in use to feel superior to prior art preparations are herein referred to as having "improved feel." One Internationally accepted benchmark for biocidal efficacy is that a specified dose of an antiseptic composition left in contact with the hands for a specified time is required to produce at least the same biocidal efficacy as 6 ml of 60% v/v isopropyl alcohol with 60 secs contact time. (The test method is fully described in European Standard EN 1500:1997, entitled 'Chemical disinfectants and antiseptics Hygienic Handrub—Test method and requirements (phase 2/step 2)' against *E. coli* NCTC 10538. hereinafter referred to as "EN1500:1997.")

Compositions for use as antiseptic hand rubs have contained materials added to "improve skin conditioning" and moisturization e.g. humectants such as glycerine, anti-inflammatories such as isolene, and anchoring agents/conditioners such as phenyldimethicone quaternary compounds. However skin "conditioners" are intended to affect the moisturization, emolliency and condition of the skin, in order to reduce irritation, rather than to affect the feel of the composition on the skin.

Any discussion of the prior art throughout the specification should in no way be considered as an admission that such prior art is widely known or forms part of common general knowledge in the field.

OBJECT OF THE INVENTION

It is an object of the present invention to overcome or ameliorate at least one of the disadvantages of the prior art, or to provide a useful alternative.

More particularly, it is an object of the present invention to provide an antiseptic handrub or handwash which avoids or ameliorates at least some of the above discussed disadvantages of prior art and which in preferred embodiments produces at least the same biocidal efficacy as is produced by hand rubbing with 6 ml of 60% v/v isopropyl alcohol in 60 seconds, but does so with improved skin feel.

Preferred embodiments are suitable for repeated use by health care personnel when moving from patient to patient or procedure to procedure with the same patient and comply with the internationally accepted standard for efficacy.

The use of preferred embodiments promotes improved compliance with antiseptic protocols.

BRIEF STATEMENT OF THE INVENTION

According to a first aspect, the invention consists in an antiseptic hand rub composition which when used at a rate of less than 6 ml of composition for up to 60 seconds produces a level of biocidal efficacy equal to or greater than that produced by 6 ml of 60% v/v aqueous isopropyl alcohol in 60 secs (as measured according to the test method of EN1500:1997), said composition characterised in that it comprises at least 0.2% w/w of isopropyl myristate.

Isopropyl myristate is the isopropyl ester of myristic acid (linear C14 saturated acid), having the following structure:

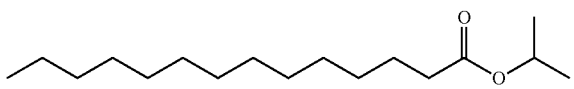 [SMILES: CCCCCCCCCCCCCC(=O)OC(C)C]

In one preferred embodiment according to the first aspect, handrubbing with only 3 ml of an ethanol based antiseptic hand rub gel composition produces in 30 seconds at least the same biocidal efficacy as is produced by hand rubbing with 6 ml of 60% v/v isopropyl alcohol in 60 seconds (as measured according to the test method of EN1500:1997). Because preferred embodiments provide the same or greater biocidal efficacy with half the quantity of the preparation and in half the time, this together with the improved feel of compositions according to the invention, greatly enhances compliance with handrubbing protocols. Since ethanol is inferior in biocidal efficacy to isopropanol it is surprising that an ethanol based antiseptic gel is as efficacious.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

In one preferred embodiment of the first aspect of the invention, the antiseptic hand rub composition is an ethanol based antiseptic hand rub composition that may comprise one or more glycols (preferably dipropylene glycol), or phenoxyethanol, or both a glycol and phenoxyethanol.

In one preferred embodiment the antiseptic is an ethanol based hand rub composition in the form of a gel.

In an alternative preferred embodiment of the first aspect of the invention, the antiseptic hand rub composition is in the form of an emulsion or dispersion that may comprise one or more glycols, of which at least one is a low molecular weight glycol (preferably propylene glycol), or phenoxyethanol, or both a glycol and phenoxyethanol.

Preferably the isopropyl myristate acts as an antipilling agent.

For preference, the isopropyl myristate is the only derivative of myristic acid present in the composition, that is, the composition is specifically free from all other esters, salts or derivatives of myristic acid such as ethyl myristate or butyl myristate, or sodium myristate, myristamide, myristyl aldehyde, myristamide DEA etc.

The isopropyl myristate acts as an anti-pilling agent and improves the feel of the composition on the skin. The present inventors have surprisingly found that inclusion of at least 0.2% w/w isopropyl myristate in alcoholic hand rubs containing glycol and phenoxyethanol (both gels and water based emulsions), significantly improves the feel otherwise produced by the same and similar compositions omitting the isopropyl myristate. Even more surprisingly, the selection of isopropyl myristate (a C14 ester) as an antipilling agent produces benefits including skin feel not obtained with the C12 or C14 isopropyl esters and also not obtained with the C16 or C18 isopropyl esters, or with other myristates.

For instance, the same highly desirable feel is not obtained by substituting the C10 isopropyl ester, isopropyl caproate (decanoate) or the C12 isopropyl ester, isopropyl laurate (dodecanoate), nor is it obtained by substituting the C16 ester isopropyl palmitate or the C18 ester isopropyl stearate. Nor by substituting other similar compositions such myristyl myristate for the isopropyl myristate Preferably the alcoholic antiseptic hand rub composition is substantially free from C10, C12, C16 or C18 isopropyl esters, i.e. free from isopropyl caproate (C10), isopropyl laurate (C12), isopropyl palmitate C16 and isopropyl stearate (C18). By substantially free is meant that the isopropyl myristate is at least 90% pure C14)

Preferably the isopropyl myristate is present in an amount of 0.1-2.0% w/w. More preferably, it may be present in an amount of 0.2-0.8% w/w, or more preferably still 0.2-0.5% w/w or 0.2-0.3% w/w.

Preferably if the alcoholic antiseptic hand rub composition is a gel then the isopropyl myristate is present in an amount of around 0.2%.

In another embodiment the invention provides a method of improving the skin feel of an ethanol based antiseptic hand rub composition which produces a level of biocidal efficacy equal to or greater than that produced by hand rubbing with 6 ml of 60% v/v isopropyl alcohol in 60 seconds (as measured in accord with EN1500:1997) applying less than 6 ml of such handrub for up to 60 seconds, said method comprising the step of incorporating at least 0.2% w/w of isopropyl myristate in the composition.

The alcoholic antiseptic hand rub composition may comprise a glycol, or phenoxyethanol or a glycol and up to 1% by wt of phenoxyethanol. In preferred embodiments it may be in the form of a gel or an emulsion or suspension.

Preferably the isopropyl myristate is added as an antipilling agent.

Preferably the isopropyl myristate is selected as the only derivative of myristic acid present in the composition and the method avoids the use of a formulation containing C10, C12, C16 or C18 isopropyl esters, i.e. the method of improving the skin feel avoids the use of isopropyl caproate (C10), isopropyl laurate (C12), isopropyl palmitate C16 and isopropyl stearate (C18).

In another aspect, the invention provides an antiseptic hand rub composition characterised in that it comprises at least 0.2% w/w of isopropyl myristate. Preferably the composition is free from any of isopropyl caproate, isopropyl laurate, isopropyl palmitate and isopropyl stearate. Preferably, isopropyl myristate is the only derivative of myristic acid present in the composition.

Preferably the isopropyl myristate is present in a concentration of from 0.2% to 0.5%

Preferably, the composition comprises phenoxyethanol. The phenoxyethanol is preferably present in a concentration of 1% by wt or less.

The composition is preferably in the form of an ethanol based hand rub or in the form of an emulsion or dispersion.

The composition preferably contains one or moreglycols.

In one preferred embodiment, the composition is an ethanol based hand rub gel, in which case the glycol is preferably dipropylene glycol. The dipropylene glycol is preferably present in an amount of from 0.25 to 4 times the amount by wt of isopropyl myristate. Preferably the dipropylene glycol is present in an amount of up to 1% by wt of the composition.

In one particularly preferred embodiment of the present invention, the invention provides a formulation comprising: ethanol, phenoxyethanol, a glycol and isopropyl myristate; and free from any other myristic acid derivative. The formulation is free from any other myristic acid derivative.

The amount of ethanol is preferably 50-80% w/w, more preferably ethanol 60-65 w/w %; the amount of dipropylene glycol is preferably 0.2-0.8% w/w, more preferably 0.4-0.6% w/w; the amount of phenoxyethanol is preferably 0.2-up to 1.0% w/w, more preferably 0.5-0.6% w/w; and the amount of isopropyl myristate is preferably 0.1 to 0.3, more preferably around 0.2% w/w.

In an alternative preferred embodiment, the composition is in the form of an emulsion or dispersion in which case at least one of the glycols is a low molecular weight glycol, preferably propylene glycol. The propylene glycol is preferably present in an amount of from 0.25 to 4 times the amount by wt of isopropyl myristate. Preferably the propylene glycol is present in an amount of up to 1% by wt of the composition.

The antiseptic compositions may include one or more additional biocides. Preferred additional biocides are triclosan and chlorhexidine gluconate.

DESCRIPTION OF PREFERRED EMBODIMENTS OF INVENTION

The formulations in examples 1 to 8 were prepared. Each formulation contains from 0.2 to 0.5% w/w of isopropyl myristate. Examples 1 to 5 below exemplify alcohol based handrub gels according to the invention. Examples 6 to 8 below exemplify water based emulsions or dispersions.

Example 1: 70% v/v Ethanol, CHG 0.5% w/w Antiseptic Gel

| | |
|---|---|
| Ethanol | 62.00% w/w |
| Chlorhexidine gluconate | 0.50% w/w |
| Hydroxypropyl methyl cellulose | 0.50% w/w |
| Glycerol | 0.50% w/w |
| Quarternium-80 | 0.05% w/w |
| Phenoxyethanol | 1.0% w/w |
| Isopropyl myristate | 0.2% w/w |
| Fragrance | 0.10% w/w |
| Aminomethylpropanol | 0.02% w/w |
| Lactic acid | 0.05% w/w |
| Red No. 33 | q.s as required |
| Deionised water | q.s to 100. |

Example 2: (70% v/v Ethanol, Triclosan 1.0% w/w Antiseptic Gel)

| | |
|---|---|
| Ethanol | 62.00% w/w |
| Triclosan | 1.00% w/w |
| Carbopol ® (polyacrylic acid polymer) | 0.40% w/w |
| Glycerol | 0.50% w/w |
| Propylene glycol | 0.50% w/w |
| Isopropyl myristate | 0.20% w/w |
| Quarternium-80 | 0.05% w/w |
| Phenoxyethanol | 1.00% w/w |
| Fragrance | q.s as required |
| Aminomethylpropanol | q.s as required |
| FD&C Green no3 | q.s as required |
| Deionised water | q.s to 100. |

Example 3: (70% v/v Ethanol Antiseptic Gel")

| | |
|---|---|
| Ethanol | 62.00% w/w |
| Carbopol ® (polyacrylic acid polymer) | 0.30% w/w |
| Dipropylene glycol | 0.50% w/w |
| Isopropyl myristate | 0.20% w/w |
| Phenoxyethanol | 0.55% w/w |
| Fragrance | q.s as required |
| Aminomethylpropanol | q.s as required |
| Dye stuff | q.s as required |

Example 4: (70% v/v Ethanol Antiseptic Gel")

| | |
|---|---|
| Ethanol | 62.00% w/w |
| Carbopol ® (polyacrylic acid polymer) | 0.35% w/w |
| Glycerol | 0.50% w/w |
| Dipropylene glycol | 0.50% w/w |
| Isopropyl myristate | 0.20% w/w |
| Quarternium 80 | 0.05% w/w |
| Phenoxyethanol | 0.50% w/w |
| Fragrance | q.s as required |
| Aminomethylpropanol | q.s as required |
| FD&C Blue No. 1 | q.s as required |
| FD&C Yellow No. 5 | q.s as required |
| Deionised water | q.s to 100 |

Example 5: 70% v/v Ethanol, CHG 2.0% w/w Surgical Gel

| | |
|---|---|
| Ethanol | 62.00% w/w |
| Chlorhexidine gluconate | 2.00% w/w |
| Hydroxy propyl methyl cellulose | 0.30% w/w |
| Glycerol | 0.50% w/w |
| Phenoxyethanol | 1.00% w/w |
| Isopropyl myristate | 0.20% w/w |
| Aminomethyl propanol | q.s as required |
| Lactic acid | q.s as required |
| Red No. 33 | q.s as required |
| Deionised water | q.s to 100. |

Examples 6-8 below are water based antiseptic emulsions or dispersions

Example 6: CHG 1% w/w Antiseptic Lotion

| | |
|---|---|
| Chlorhexidine gluconate | 1.00% w/w |
| Cetostearayl alcohol | 2.50% w/w |
| Cetyl palmitate | 0.50% w/w |
| Ceteareth 20 | 0.60% w/w |
| POE-40 hydrogenated castor oil | 0.20% w/w |
| Polyethylen glycol-4000 | 2.70% w/w |
| Glyceryl stearate | 0.50% w/w |
| PEG-100 stearate | 0.50% w/w |
| Sorbitan monostearate | 0.70% w/w |
| Paraffin oil | 4.00% w/w |
| Isopropyl myristate | 0.50% w/w |
| Phenoxyethanol | 1.00% w/w |
| Ethanol | 5.00% w/w |
| Propylene glycol | 0.50% w/w |
| PEG-150/stearyl alcohol/SMDI copolymer | 4.00% w/w |
| Barium sulphate | 2.00% w/w |
| Quarternium 80 | 0.20% w/w |
| Fragrance | 0.05% w/w |
| Deionised water | q.s to 100. |

Example 7: CHG 2% w/w Surgical Lotion

| | |
|---|---|
| Chlorhexidine gluconate | 2.00% w/w |
| Cetosterayl alcohol | 1.80% w/w |
| Cetyl palmitate | 0.50% w/w |
| Ceteareth 20 | 0.60% w/w |
| POE-40 hydrogenated castor oil | 0.20% w/w |
| Polyethylen glycol-4000 | 1.80% w/w |
| Glyceryl stearate | 0.40% w/w |
| PEG-100 stearate | 0.40% w/w |
| Sorbitan monostearate | 0.40% w/w |
| Paraffin oil | 3.0% w/w |
| Isopropyl myristate | 1.00% w/w |
| Phenoxyethanol | 1.00% w/w |
| Ethanol | 10.00% w/w |
| Propylene glycol | 0.50% w/w |
| PEG-150/stearyl alcohol/SMDI copolymer | 2.00% w/w |
| Barium sulphate | 2.00% w/w |
| Quarternium 80 | 0.20% w/w |
| Deionised water | q.s to 100. |

Example 8: Triclosan 0.5% w/w Antiseptic Lotion

| | |
|---|---|
| Triclosan | 0.50% w/w |
| Cetosterayl alcohol | 2.50% w/w |
| Cetyl palmitate | 0.50% w/w |
| Ceteareth 20 | 0.60% w/w |
| POE-40 hydrogenated castor oil | 0.20% w/w |
| Polyethylen glycol-4000 | 2.70% w/w |
| Glyceryl stearate | 0.50% w/w |
| PEG-100 stearate | 0.50% w/w |
| Sorbitan monostearate | 0.70% w/w |
| Paraffin oil | 4.00% w/w |
| Isopropyl myristate | 0.50% w/w |
| Phenoxyethanol | 1.00% w/w |
| Chlorhexidine gluconate | 0.20% w/w |
| Ethanol | 5.00% w/w |
| Propylene glycol | 0.50% w/w |
| Povidone | 0.20% w/w |
| PEG-150/stearyl alcohol/SMDI copolymer | 2.00% w/w |
| Barium sulphate | 2.00% w/w |
| Quarternium 80 | 0.20% w/w |
| Fragrance | 0.05% w/w |
| Deionised water | q.s to 100. |

Method—Part 1 Tests A, B, C—Relating to Ethanol Based Antiseptic Hand Rub Gels
Comparative Tests as to Skin Feel were Conducted as Follows:

Various alcoholic gel antiseptic formulations based on Example 3 were prepared with the isopropyl myristate removed from the formulation which was otherwise left intact and various isopropyl esters, myristyl myristate, glycerol laurate—all of which are considered to be emollients. These and a market leading alcoholic gel antiseptic were compared by an experienced panel for their skin feel after repeated usage.

A. The ethanol antiseptic gel formula described in Example 3 above was used to prepare skin feel test formulations as follows:
1. Omitting the isopropyl myristate without replacement.
2. Omitting the isopropyl myristate; replacing the isopropyl myristate in Example 3 with the C10 Isopropyl ester.
3. Omitting the isopropyl myristate; replacing the isopropyl myristate in Example 3 with the C12 Isopropyl ester.
4. Incorporating isopropyl myristate.
5. Omitting the isopropyl myristate; replacing the isopropyl myristate in Example 3 with the C16 Isopropyl ester.
6. Omitting the isopropyl myristate; replacing the isopropyl myristate in Example 3 with the C18 Isopropyl ester.
7. Omitting the isopropyl myristate; replacing the isopropyl myristate in Example 3 with myristyl myristate.
8. Omitting the isopropyl myristate; replacing the isopropyl myristate in Example 3 with glyceryl laurate.
9. Alcoholic hand rub "Angel"® from Johnson and Johnson.

B. Various Levels of isopropyl myristate. The ethanol antiseptic gel formula described in Example 3 above was used to prepare skin feel test formulations as follows:
1. The formulation without isopropyl myristate.
2. The formulation with 0.1% w/w isopropyl myristate.
3. The formulation with 0.2% w/w isopropyl myristate.
4. The formulation with 0.35% w/w isopropyl myristate.
5. The formulation with 0.5% w/w isopropyl myristate.
6. The formulation with 0.8% w/w isopropyl myristate.

C. Various Levels of glycol, in this case dipropylene glycol (DPG) were added to Example 3 which otherwise was unchanged and these assessed for skin feel. The levels of dipropylene glycol (DPG) added to Example 3 were:
1. The formulation with 0.1% w/w Dipropylene glycol
2. The formulation with 0.5% w/w Dipropylene glycol
3. The formulation with 0.8% w/w Dipropylene glycol
4. The formulation with 1.0% w/w Dipropylene glycol
5. The formulation with 1.3% w/w Dipropylene glycol The hands were first washed with antiseptic handwash following standard hospital handwash procedure and dried with paper towels and then allowed to dry for 5 minutes. 3 ml of the respective test product was then applied to both hands and rubbed until dry. After a further minute skin feel was noted. After 5 minutes from the first application, a second application of the test product was applied to both hands and the test procedure was repeated. This sequence was repeated until 4 further 3 ml applications had been made with 5 minute intervals between each. The skin feel and pilling were both noted 1 minute after the hands were rubbed dry after the 5$^{th}$ application.

The tests were conducted with a panel of 10 experienced staff on 3 occasions, each at a different site. The results were as follows: "IPM" refers to isopropyl myristate. "DPG" refers to dipropylene glycol.

The respondents were able to choose from a limited number of descriptive results with a sufficient range of choices to encompass the full spectrum of possible results. The respondents were asked to classify the feel as "light" or "heavy" and to classify the feel as one or more of "dry" or "smooth" or "waxy", "greasy" or "oily". In the results columns the number of respondents providing the predominant skin feel result ("res") were noted.

Method—Part 2 Tests D, E, F Relating to Antiseptic Handrub Emulsions/Suspensions Various aqueous emulsion (lotion) antiseptic formulations were prepared with the isopropyl myristate removed from the formulation which was otherwise left intact and various Isopropyl esters, myristyl myristate, glycerol laurate—all of which are considered to be emollients. These were compared by an experienced panel for their skin feel after repeated usage.

D. The aqueous antiseptic emulsion formula described in Example 8 above was used to prepare skin feel test formulations as follows:
1. Omitting the isopropyl myristate without replacement.
2. Omitting the isopropyl myristate; replacing the Isopropyl myristate in Example 8 with the C10 isopropyl ester.

3. Omitting the isopropyl myristate; replacing the Isopropyl myristate in Example 8 with the C12 isopropyl ester.
4. Incorporating isopropyl myristate.
5. Omitting the isopropyl myristate; replacing the Isopropyl myristate in Example 8 with the C16 Isopropyl ester.
6. Omitting the isopropyl myristate; replacing the Isopropyl myristate in Example 8 with the C18 Isopropyl ester.
7. Omitting the isopropyl myristate; replacing the Isopropyl myristate in Example 8 with myristyl myristate.
8. Omitting the isopropyl myristate; replacing the Isopropyl myristate in Example 8 with glyceryl laurate.

E. Various Levels of Isopropyl Myristate:

The aqueous antiseptic emulsion formula described in Example 8 above was used to prepare skin feel test formulations as follows:
1. The formulation without isopropyl myristate.
2. The formulation with 0.2% w/w isopropyl myristate.
3. The formulation with 0.5% w/w isopropyl myristate.
4. The formulation with 0.8% w/w isopropyl myristate.
5. The formulation with 1.0% w/w isopropyl myristate.
6. The formulation with 1.3% w/w isopropyl myristate.

F Various Levels of Glycol, in this case propylene glycol (PG), were added to Example 8 which otherwise was unchanged and these assessed for skin feel:
1. The formulation with 0.2% w/w propylene glycol.
2. The formulation with 0.5% w/w propylene glycol.
3. The formulation with 0.8% w/w propylene glycol.
4. The formulation with 1.0% w/w propylene glycol.
5. The formulation with 1.3% w/w propylene glycol.

The hands were first washed with antiseptic handwash following standard hospital handwash procedure and dried with paper towels and then allowed to dry for 5 minutes. 4 ml of the respective test product was then applied to both hands and rubbed until dry. After a further minute skin feel was noted. After 5 minutes from the first application, a second application of the test product was applied to both hands and the test procedure was repeated. This sequence was repeated until 2 further 4 ml applications had been made with 5 minute intervals between each. The skin feel was both noted 1 minute after the hands were rubbed dry after the 3$^{rd}$ application.

The tests were conducted with a panel of 10 experienced staff on 3 occasions, each at a different site. The results were as follows: "IPM" refers to isopropyl myristate "PG" refers to propylene glycol.

In the results columns the number of respondents providing the predominant skin feel result were noted.

The respondents were able to choose from a limited number of descriptive results with a sufficient range of choices to encompass the full spectrum of possible results.

Results—Part 1 Tests A, B, C—Relating to Ethanol Based Antiseptic Hand Rub Gels

Tests to date have shown that the biocidal efficacy of compositions according to the invention was not adversely affected by inclusion of isopropyl myristate (IPM) in amounts of up to at least 1% w/w.

For example, an alcoholic hand rub according to example 3 of the invention complies with the requirements of the European standard test with a log reduction of 3.29 after 30 seconds rubbing with 3 mL of product compared to the reference product, 6 mL (60% v/v Propan-2-ol) for 60 seconds contact time with a log reduction of 3.33. (a difference in log reduction of no statistical significance despite the difference in quantity and time)

TABLE 1

Results from Test A, Site 1
Effect of various isopropyl esters on Skin Feel in comparison with market leading product

| | After 1$^{st}$ Application | Res. | After 5$^{th}$ Application | Res. | Pilling | Res. | Rank |
|---|---|---|---|---|---|---|---|
| Example 3 without IPM | Light, Dry | 7/10 | Light, Very Dry | 8/10 | Pilling a lot | 9/10 | 5 |
| Example 3 with IPM (C14) | Light, smooth | 6/10 | Soft, Smooth | 8/10 | No Pilling | 8/10 | 1 |
| Example 3 with C10 | Light, Dry | 8/10 | Light, Very Dry | 7/10 | Pilling a bit | 8/10 | 2 |
| Example 3 with C12 | Light, Dry | 7/10 | Light, Dry | 6/10 | Pilling a bit | 7/10 | 2 |
| Example 3 with C16 | Heavy, Waxy | 8/10 | Heavy, Waxy | 8/10 | No Pilling | 7/10 | 3 |
| Example 3 with C18 | Heavy, Waxy | 7/10 | Heavy, Oily & Waxy | 9/10 | No Pilling | 8/10 | 4 |
| Example 3 with Myristyl Myristate | Heavy, Waxy | 7/10 | Heavy, Waxy | 6/10 | No Pilling | 7/10 | 6 |
| Example 3 with Glyceryl Laurate | Heavy, Greasy | 7/10 | Heavy, Greasy | 8/10 | No Pilling | 9/10 | 6 |
| Example with "Angel" ® | Light, smooth, Oily | 8/10 | Greasy, Very Oily | 7/10 | Pilling a lot | 9/10 | 8 |

From the results of above Table 1 it has been concluded that:

1. After repeated cycles of use the composition incorporating isopropyl myristate produced skin feel preferred to that produced by any of the other Isopropyl ester containing compositions tested.

2. After repeated cycles of use the composition incorporating isopropyl myristate produced the preferred combination of skin feel in combination with minimal pilling than the other compositions tested.

TABLE 2

Test B - Site 1
Effect of IPM concentration on Skin Feel

|  | After 1st Application | No. | After 5th Application | No. | Pilling | No. | Rank |
|---|---|---|---|---|---|---|---|
| Example 3 without IPM | Light, Dry | 7/10 | Light, Very Dry | 8/10 | Pilling a lot | 9/10 | 6 |
| Example 3 with 0.1% IPM | Light, Very Dry | 8/10 | Light, Dry | 8/10 | Pilling a bit | 9/10 | 4 |
| Example 3 with 0.2% IPM | Light, Smooth | 6/10 | Soft, Smooth | 8/10 | No Pilling | 8/10 | 1 |
| Example 3 with 0.35% IPM | Light, Smooth | 9/10 | Soft, Smooth, Oily | 6/10 | No Pilling | 9/10 | 2 |
| Example 3 with 0.5% IPM | Soft, Smooth | 6/10 | Soft, Oily | 8/10 | No Pilling | 8/10 | 2 |
| Example 3 with 0.8% IPM | Soft, Smooth | 8/10 | Heavy, Oily | 9/10 | No Pilling | 9/10 | 4 |

From the results of above Table 2 it has been concluded that:
Of the various levels of isopropyl myristate added to the composition, after repeated cycles of use, the test subjects preferred the compositions incorporating isopropyl myristate at levels of 0.2%, 0.35% and 0.5%. Of these the level of 0.2% was somewhat preferred over the levels of 0.35% and 0.5%.

TABLE 3

Test C - Site 1
Effect of Dipropylene glycol concentration on Skin Feel

|  | After 1st Application | No. | After 5th Application | No. | Pilling | No. | Rank |
|---|---|---|---|---|---|---|---|
| Example 3 with 0.2% DPG and 0.2% IPM | Light, Very Dry | 7/10 | Light, Dry | 8/10 | Pilling a bit | 8/10 | 5 |
| Example 3 with 0.5% DPG and 0.2% IPM | Light, Smooth | 6/10 | Soft, Smooth | 8/10 | No Pilling | 8/10 | 1 |
| Example 3 with 0.8% DPG and 0.2% IPM | Light, Smooth | 6/10 | Soft, Smooth | 8/10 | No Pilling | 8/10 | 1 |
| Example 3 with 1% DPG and 0.2% IPM | Light, Smooth | 7/10 | Soft, Tacky | 7/10 | No Pilling | 9/10 | 3 |
| Example 3 with 1.3% DPG and 0.2% IPM | Light, Tacky | 6/10 | Heavy, Tacky | 8/10 | No Pilling | 9/10 | 4 |

From the results of above Table 3 it has been concluded that:
Of the various levels of dipropylene glycol added to the composition, after repeated cycles of use, the test subjects preferred the compositions incorporating dipropylene glycol at levels of 0.5%, 0.8% and 1.0%. Of these the level of 0.5% was somewhat preferred over the levels of 0.8% and 1.0%.

TABLE 4

Results from Test A, Site 2
Effect of various isopropyl esters on Skin Feel in comparison with market leading product

|  | After 1st Application | No. | After 5th Application | No. | Pilling | No. | Rank |
|---|---|---|---|---|---|---|---|
| Example 3 without IPM | Light, Dry | 9/10 | Light, Very Dry | 8/10 | Pilling a lot | 6/10 | 6 |
| Example 3 with IPM (C14) | Light, smooth | 8/10 | Soft, Smooth | 9/10 | No Pilling | 8/10 | 1 |
| Example 3 with C10 | Light, Dry | 7/10 | Light, Dry | 7/10 | Pilling a bit | 6/10 | 2 |
| Example 3 with C12 | Light, Dry | 8/10 | Light, Dry | 6/10 | Pilling a bit | 7/10 | 3 |
| Example 3 with C16 | Heavy, Oily | 9/10 | Heavy, Oily | 9/10 | No Pilling | 8/10 | 3 |
| Example 3 with C18 | Heavy, Waxy | 8/10 | Heavy, Oily & Waxy | 8/10 | No Pilling | 7/10 | 5 |
| Example 3 with Myristyl Myristate | Heavy, Waxy | 7/10 | Heavy, Waxy | 7/10 | No Pilling | 8/10 | 7 |
| Example 3 with Glyceryl Laurate | Heavy, Greasy | 6/10 | Heavy, Greasy | 8/10 | No Pilling | 8/10 | 8 |
| Example with "Angel" ® | Light, smooth, Oily | 9/10 | Greasy, Very Oily | 8/10 | Pilling a lot | 9/10 | 8 |

From the results of above Table 4 it has been concluded that:
1. After repeated cycles of use the composition incorporating isopropyl myristate produced skin feel preferred to that produced by any of the other Isopropyl ester containing compositions tested.
2. After repeated cycles of use the composition incorporating isopropyl myristate produced the preferred combination of skin feel in combination with minimal pilling as compared to the other compositions tested.

TABLE 5

Test B, Site 2
Effect of IPM concentration on Skin Feel

|  | After 1st Application | No. | After 5th Application | No. | Pilling | No. | Rank |
|---|---|---|---|---|---|---|---|
| Example 3 without IPM | Light, Dry | 9/10 | Light, Very Dry | 8/10 | Pilling a lot | 6/10 | 6 |
| Example 3 with 0.1% IPM | Light, Very Dry | 8/10 | Light, Dry | 8/10 | Pilling a bit | 8/10 | 4 |
| Example 3 with 0.2% IPM | Light, Smooth | 8/10 | Soft, Smooth | 9/10 | No Pilling | 8/10 | 1 |
| Example 3 with 0.35% IPM | Light, Smooth | 8/10 | Soft, Smooth, Oily | 6/10 | Pilling a bit | 7/10 | 2 |
| Example 3 with 0.5% IPM | Soft, Smooth | 7/10 | Soft, Oily | 8/10 | No Pilling | 6/10 | 2 |
| Example 3 with 0.8% IPM | Soft, Smooth | 7/10 | Heavy, Oily | 7/10 | No Pilling | 7/10 | 4 |

From the results of above Table 5 it has been concluded that:
Of the various levels of isopropyl myristate added to the composition, after repeated cycles of use the test subjects preferred the compositions incorporating isopropyl myristate at levels of 0.2%, 0.35% and 0.5%. Of these the level of 0.2% was somewhat preferred over the levels of 0.35% and 0.5%.

TABLE 6

Test C, Site 2
Effect of Dipropylene glycol concentration on Skin Feel

|  | After 1st Application | No. | After 5th Application | No. | Pilling | No. | Rank |
|---|---|---|---|---|---|---|---|
| Example 3 with 0.2% DPG and 0.2% IPM | Light, Very Dry | 8/10 | Light, Dry | 8/10 | Pilling a bit | 7/10 | 5 |
| Example 3 with 0.5% DPG and 0.2% IPM | Light, Smooth | 8/10 | Soft, Smooth | 9/10 | No Pilling | 8/10 | 1 |
| Example 3 with 0.8% DPG and 0.2% IPM | Light, Smooth | 6/10 | Soft, Smooth | 7/10 | No Pilling | 9/10 | 2 |
| Example 3 with 1% DPG and 0.2% IPM | Light, Smooth | 8/10 | Soft, Tacky | 7/10 | No Pilling | 7/10 | 2 |
| Example with 1.3% DPG and 0.2% IPM | Light, Tacky | 7/10 | Heavy, Tacky | 8/10 | No Pilling | 9/10 | 4 |

From the results of above Table 6 it has been concluded that:
Of the various levels of dipropylene glycol added to the composition, after repeated cycles of use the test subjects preferred the compositions incorporating dipropylene glycol at levels of 0.5%, 0.8% and 1.0%. Of these the level of 0.5% was somewhat preferred over the levels of 0.8% and 1.0%.

TABLE 7

Results from Test A, Site 3
Effect of various isopropyl esters on Skin Feel in comparison with market leading product

|  | After 1st Application | No. | After 5th Application | No. | Pilling | No. | Rank |
|---|---|---|---|---|---|---|---|
| Example 3 without IPM | Light, Dry | 9/10 | Light, Very Dry | 8/10 | Pilling a lot | 9/10 | 5 |
| Example 3 with IPM (C14) | Light, smooth | 8/10 | Soft, Smooth | 6/10 | No Pilling | 8/10 | 1 |

TABLE 7-continued

Results from Test A, Site 3
Effect of various isopropyl esters on Skin Feel in comparison with market leading product

|  | After 1st Application | No. | After 5th Application | No. | Pilling | No. | Rank |
|---|---|---|---|---|---|---|---|
| Example 3 with C10 | Light, Dry | 7/10 | Light, Very Dry | 6/10 | Pilling a bit | 8/10 | 2 |
| Example 3 with C12 | Light, Dry | 8/10 | Light, Smooth | 6/10 | Pilling a bit | 7/10 | 2 |
| Example 3 with C16 | Light, Smooth | 9/10 | Heavy, Oily | 7/10 | No Pilling | 9/10 | 2 |
| Example 3 with C18 | Heavy, Waxy | 6/10 | Heavy, Oily | 8/10 | No Pilling | 9/10 | 5 |
| Example 3 with Myristyl Myristate | Heavy, Waxy | 8/10 | Heavy, Waxy | 9/10 | No Pilling | 8/10 | 7 |
| Example 3 with Glyceryl Laurate | Heavy, Greasy | 7/10 | Heavy, Greasy | 6/10 | No Pilling | 8/10 | 7 |
| Example with "Angel" ® | Light, smooth, Oily | 9/10 | Greasy, Very Oily | 8/10 | Pilling a lot | 9/10 | 8 |

From the results of above Table 7 it has been concluded that:
1. After repeated cycles of use the composition incorporating isopropyl myristate produced skin feel preferred to that produced by any of the other Isopropyl ester containing compositions tested.
2. After repeated cycles of use the composition incorporating isopropyl myristate produced the preferred combination of skin feel in combination with minimal pilling as compared to the other compositions tested.

TABLE 8

Test B, Site 3
Effect of IPM concentration on Skin Feel

|  | After 1st Application | No. | After 5th Application | No. | Pilling | No. | Rank |
|---|---|---|---|---|---|---|---|
| Example 3 without IPM | Light, Dry |  | 9/10 | Light, Very Dry | 8/10 | Pilling a lot | 9/10 | 6 |
| Example 3 with 0.1% IPM | Light, Very Dry | 8/10 | Light, Dry | 8/10 | Pilling a bit | 8/10 | 4 |
| Example 3 with 0.2% IPM | Light, smooth | 8/10 | Soft, Smooth | 6/10 | No Pilling | 8/10 | 1 |
| Example 3 with 0.35% IPM | Light, Smooth | 8/10 | Soft, Smooth, Oily | 6/10 | Pilling a bit | 7/10 | 2 |
| Example 3 with 0.5% IPM | Soft, Smooth | 8/10 | Soft, Oily | 9/10 | No Pilling | 8/10 | 2 |
| Example 3 with 0.8% IPM | Soft, Smooth | 7/10 | Heavy, Oily | 9/10 | No Pilling | 7/10 | 4 |

From the results of above Table 8 it has been concluded that:
Of the various levels of isopropyl myristate added to the composition, after repeated cycles of use the test subjects preferred the compositions incorporating isopropyl myristate at levels of 0.2%, 0.35% and 0.5%. Of these the level of 0.2% was somewhat preferred over the levels of 0.35% and 0.5%.

TABLE 9

Test C, Site 3
Effect of Dipropylene glycol concentration on Skin Feel

|  | After 1st Application | No. | After 5th Application | No. | Pilling | No. | Rank |
|---|---|---|---|---|---|---|---|
| Example 3 with 0.2% DPG and 0.2% IPM | Light, Very Dry | 9/10 | Light, Dry | 8/10 | Pilling a bit | 7/10 | 5 |
| Example 3 with 0.5% DPG and 0.2% IPM | Light, smooth | 8/10 | Soft, Smooth | 6/10 | No Pilling | 8/10 | 1 |
| Example 3 with 0.8% DPG and 0.2% IPM | Light, Smooth | 7/10 | Soft, Smooth | 7/10 | No Pilling | 7/10 | 2 |

TABLE 9-continued

Test C, Site 3
Effect of Dipropylene glycol concentration on Skin Feel

| | After 1st Application | No. | After 5th Application | No. | Pilling | No. | Rank |
|---|---|---|---|---|---|---|---|
| Example 3 with 1% DPG and 0.2% IPM | Light, Smooth | 8/10 | Soft, Tacky | 9/10 | No Pilling | 7/10 | 2 |
| Example 3 with 1.3% DPG and 0.2% IPM | Light, Tacky | 7/10 | Heavy, Tacky | 9/10 | No Pilling | 9/10 | 4 |

From the results of above Table 9 it has been concluded that:

Of the various levels of dipropylene glycol added to the composition, after repeated cycles of use the test subjects preferred the compositions incorporating dipropylene glycol at levels of 0.5%, 0.8% and 1.0%. Of these the level of 0.5% was somewhat preferred over the levels of 0.8% and 1.0%.

Consolidated Conclusions Across the Tests A, B, C and Sites 1-3

It is notable that for Tests A, B and C the preferred compositions chosen by the panellists at each of the sites were the same. This consistency of results is indicative of the experience of the panellists and clearly discernible differences in the results.

Test A

The majority of panellists across the three sites agreed on the composition with the preferred emollient with respect to skin feel and pilling. Their clear choice was the formulation with isopropyl myristate.

Test B

The majority of panellists agreed that the feel of the formula with IPM was significantly better than that of any other tested formulation. This was the case not only after the first application but more so after repeated applications. Similar results were obtained with the other formulations exemplified and at a range of isopropyl myristate concentrations up to 0.5% w/w and the most preferred level of isopropyl myristate was 0.2%.

As will be understood by those skilled in the art the antiseptic compositions can be formulated using other components and in other concentrations without departing from the inventive concept herein disclosed of incorporating isopropyl myristate to improve the feel of the product and enhance its propensity to be used.

Test C

As for Test A the majority of panellists agreed on a composition with a preferred level of dipropylene glycol with respect to skin feel and pilling. The results were consistent across the cycles of use. The preferred composition incorporated dipropylene glycol at a level of 0.5%.

Results—Part 2 Tests D, E, F Relating to Antiseptic Hand Rub Emulsions and Dispersions The aqueous hand rub (lotion) according to the invention complies with the requirements of the European standard test with a log reduction of 3.77 after 60 seconds rubbing with 4 mL of product compared to the reference product, 6 mL (60% v/v propan-2-ol) for 60 seconds contact time with a log reduction of 4.04. (a difference in log reduction of no statistical significance despite the difference in quantity and time)

TABLE 10

Results from Test D, Site 1
SKIN FEEL Comparison with various Isopropyl esters

| | After 1st Application | Res. | After 3rd Application | Res. | Rank |
|---|---|---|---|---|---|
| Example 8 without IPM | Light, Dry | 7/10 | Light, Dry | 7/10 | 3 |
| Example 8 with IPM (C14) | Light, Smooth | 6/10 | Soft, Smooth | 7/10 | 1 |
| Example 8 with C10 | Light, Dry | 8/10 | Light, Dry | 8/10 | 3 |
| Example 8 with C12 | Light, Dry | 7/10 | Light, Smooth | 8/10 | 2 |
| Example 8 with C16 | Heavy, Smooth | 9/10 | Heavy, Waxy | 8/10 | 5 |
| Example 8 with C18 | Heavy, Waxy | 7/10 | Heavy, Oily & Waxy | 7/10 | 5 |
| Example 8 with Myristyl Myristate | Heavy, Waxy | 7/10 | Heavy, Waxy | 8/10 | 7 |
| Example 8 with Glyceryl Laurate | Heavy, Greasy | 7/10 | Heavy, Greasy | 7/10 | 8 |

From the above Table 10 results it has been concluded that:

After repeated cycles of use the composition incorporating isopropyl myristate produced skin feel preferred to that produced by any of the other isopropyl ester containing compositions tested.

TABLE 11

Results from Test D, Site 2
SKIN FEEL Comparison with various Isopropyl esters

| | After 1st Application | No. | After 3rd Application | No. | Rank |
|---|---|---|---|---|---|
| Example 8 without IPM | Light, Dry | 6/10 | Light, Dry | 8/10 | 4 |
| Example 8 with IPM (C14) | Light, Smooth | 8/10 | Soft, Smooth | 7/10 | 1 |
| Example 8 with C10 | Light, Dry | 7/10 | Light, Dry | 7/10 | 2 |
| Example 8 with C12 | Light, Dry | 7/10 | Light, Smooth | 8/10 | 2 |
| Example 8 with C16 | Heavy, Smooth | 8/10 | Heavy, Waxy | 6/10 | 5 |
| Example 8 with C18 | Heavy, Waxy | 7/10 | Heavy, Oily & Waxy | 8/10 | 6 |
| Example 8 with Myristyl Myristate | Heavy, Waxy | 7/10 | Heavy, Waxy | 9/10 | 7 |
| Example 8 with Glyceryl Laurate | Heavy, Greasy | 7/10 | Heavy, Greasy | 7/10 | 7 |

From the above Table 11 results it has been concluded that:

After repeated cycles of use the composition incorporating isopropyl myristate produced skin feel preferred to that produced by any of the other isopropyl ester containing compositions tested.

TABLE 12

Results from Test D, Site 3
SKIN FEEL Comparison with various Isopropyl esters

|  | After 1$^{st}$ Application | No. | After 3$^{rd}$ Application | No. | Rank |
|---|---|---|---|---|---|
| Example 8 without IPM | Light, Dry | 9/10 | Light, Dry | 8/10 | 2 |
| Example 8 with IPM (C14) | Light, Smooth | 8/10 | Soft, Smooth | 8/10 | 1 |
| Example 8 with C10 | Light, Dry | 6/10 | Light, Dry | 7/102 | 2 |
| Example 8 with C12 | Light, Dry | 7/10 | Light, Smooth | 7/10 | 4 |
| Example 8 with C16 | Heavy, Smooth | 8/10 | Heavy, Waxy | 7/10 | 5 |
| Example 8 with C18 | Heavy, Waxy | 7/10 | Heavy, Oily & Waxy | 7/10 | 5 |
| Example 8 with Myristyl Myristate | Heavy, Waxy | 7/10 | Heavy, Waxy | 8/10 | 7 |
| Example 8 with Glyceryl Laurate | Heavy, Greasy | 7/10 | Heavy, Greasy | 7/10 | 7 |

From the above Table 12 results it has been concluded that:

After repeated cycles of use the composition incorporating isopropyl myristate produced skin feel preferred to that produced by any of the other isopropyl ester containing compositions tested.

TABLE 13

Test E - Site 1
Effect on feel of varying IPM concentration

|  | After 1$^{st}$ Application | No. | After 3$^{rd}$ Application | No. | Rank |
|---|---|---|---|---|---|
| Example 8 without IPM | Light, Dry | 6/10 | Light, Dry | 8/10 | 6 |
| Example 8 with 0.2% IPM | Light, Dry | 7/10 | Light, Dry/Smooth | 8/10 | 2 |
| Example 8 with 0.5% IPM | Light, Smooth | 6/10 | Soft, Smooth | 7/10 | 1 |
| Example 8 with 0.8% IPM | Soft, Smooth | 7/10 | Soft, Smooth, Oily | 6/10 | 2 |
| Example 8 with 1.0% IPM | Soft, Smooth | 6/10 | Heavy, Oily | 8/10 | 2 |
| Example 8 with 1.3% IPM | Heavy, Smooth | 8/10 | Heavy, Oily | 7/10 | 5 |

From the above Table 13 results it has been concluded that:

Of the various levels of isopropyl myristate added to the composition, after repeated cycles of use the test subjects preferred the compositions incorporating isopropyl myristate at levels of 0.5%, 0.8% and 1.0%. Of these the level of 0.5% was somewhat preferred over the levels of 0.8% and 1.0%.

TABLE 14

Test E, Site 2
Effect on feel of varying IPM concentration

| Effect on feel of varying IPM concentration | After 1$^{st}$ Application | No. | After 3$^{rd}$ Application | No. | Rank |
|---|---|---|---|---|---|
| Example 8 without IPM | Light, Dry | 6/10 | Light, Dry | 8/10 | 6 |
| Example 8 with 0.2% IPM | Light, Dry | 7/10 | Light, Dry/Smooth | 7/10 | 5 |
| Example 8 with 0.5% IPM | Light, Smooth | 6/10 | Soft, Smooth | 7/10 | 1 |
| Example 8 with 0.8% IPM | Soft, Smooth | 9/10 | Soft, Smooth, Oily | 7/10 | 1 |
| Example 8 with 1.0% IPM | Soft, Smooth | 8/10 | Heavy, Oily | 8/10 | 3 |
| Example 8 with 1.3% IPM | Heavy, Smooth | 7/10 | Heavy, Oily | 9/10 | 4 |

From the above Table 14 results it has been concluded that:

Of the various levels of isopropyl myristate added to the composition, after repeated cycles of use the test subjects preferred the compositions incorporating isopropyl myristate at levels of 0.5%, 0.8% and 1.0%. Of these the level of 0.5% was somewhat preferred over the levels of 0.8% and 1.0%.

TABLE 15

Test E, Site 3
Effect on feel of varying IPM concentration

|  | After 1$^{st}$ Application | No. | After 3$^{rd}$ Application | No. | Rank |
|---|---|---|---|---|---|
| Example 8 without IPM | Light, Dry | 9/10 | Light, Dry | 8/10 | 5 |
| Example 8 with 0.2% IPM | Light, Dry | 8/10 | Light, Dry/Smooth | 6/10 | 4 |
| Example 8 with 0.5% IPM | Light, Smooth | 8/10 | Soft, Smooth | 8/10 | 1 |
| Example 8 with 0.8% IPM | Soft, Smooth | 7/10 | Soft, Smooth, Oily | 7/10 | 2 |
| Example 8 with 1.0% IPM | Soft, Smooth | 6/10 | Heavy, Oily | 7/10 | 2 |
| Example 8 with 1.3% IPM | Heavy, Smooth | 7/10 | Heavy, Oily | 8/10 | 6 |

From the above Table 15 results it has been concluded that:

Of the various levels of isopropyl myristate added to the composition, after repeated cycles of use the test subjects preferred the compositions incorporating isopropyl myristate at levels of 0.5%, 0.8% and 1.0%. Of these the level of 0.5% was somewhat preferred over the levels of 0.8% and 1.0%.

TABLE 16

Test F - Site 1
Effect on Feel of variation in level of Propylene Glycol

|  | After 1$^{st}$ Application | No. | After 3$^{rd}$ Application | No. | Rank |
|---|---|---|---|---|---|
| Example 8 with 0.2% PG and 0.5% IPM | Light, Dry | 7/10 | Light, Dry/Smooth | 7/10 | 4 |

TABLE 16-continued

Test F - Site 1
Effect on Feel of variation in level of Propylene Glycol

|  | After 1st Application | No. | After 3rd Application | No. | Rank |
|---|---|---|---|---|---|
| Example 8 with 0.5% PG and 0.5% IPM | Light, Smooth | 6/10 | Soft, Smooth | 7/10 | 1 |
| Example 8 with 0.8% PG and 0.5% IPM | Soft, Smooth | 6/10 | Soft, Smooth, a bit tacky | 7/10 | 1 |
| Example 8 with 1% PG and 0.5% IPM | Soft, Smooth | 8/10 | Soft, Tacky | 7/10 | 3 |
| Example 8 with 1.3% PG and 0.5% IPM | Soft, Tacky | 6/10 | Heavy, Tacky | 7/10 | 4 |

From the above Table 16 results it has been concluded that:
Of the various levels of propylene glycol added to the composition, after repeated cycles of use the test subjects preferred the compositions incorporating propylene glycol at levels of 0.5%, 0.8% and 1.0%. Of these the level of 0.5% was somewhat preferred over the levels of 0.8% and 1.0%.

TABLE 17

Test F, Site 2
Effect on feel of variation in level of Propylene Glycol

|  | After 1st Application | No. | After 3rd Application | No. | Rank |
|---|---|---|---|---|---|
| Example 8 with 0.2% PG and 0.5% IPM | Light, Dry | 7/10 | Light, Dry/Smooth | 8/10 | 5 |
| Example 8 with 0.5% PG and 0.5% IPM | Light, Smooth | 6/10 | Soft, Smooth | 7/10 | 1 |
| Example 8 with 0.8% PG and 0.5% IPM | Soft, Smooth | 6/10 | Soft, Smooth, a bit tacky | 8/10 | 2 |
| Example 8 with 1% PG and 0.5% IPM | Soft, Smooth | 7/10 | Soft, Tacky | 7/10 | 2 |
| Example 8 with 1.3% PG and 0.5% IPM | Soft, Tacky | 6/10 | Heavy, Tacky | 8/10 | 4 |

From the above Table 17 results it has been concluded that:
Of the various levels of propylene glycol added to the composition, after repeated cycles of use the test subjects preferred the compositions incorporating propylene glycol at levels of 0.5%, 0.8% and 1.0%. Of these the level of 0.5% was somewhat preferred over the levels of 0.8% and 1.0%.

TABLE 18

Test F, Site 3
Effect on feel of variation in level of Propylene Glycol

|  | After 1st Application | No. | After 3rd Application | No. |
|---|---|---|---|---|
| Example 8 with 0.2% PG and 0.5% IPM | Light, Dry | 7/10 | Light, Dry/Smooth | 7/10 |
| Example 8 with 0.5% PG and 0.5% IPM | Light, Smooth | 8/10 | Soft, Smooth | 8/10 |
| Example 8 with 0.8% PG and 0.5% IPM | Soft, Smooth | 8/10 | Soft, Smooth, a bit tacky | 7/10 |
| Example 8 with 1% PG and 0.5% IPM | Soft, Smooth | 8/10 | Soft, Tacky | 7/10 |
| Example 8 with 1.3% PG and 0.5% IPM | Soft, Tacky | 6/10 | Heavy, Tacky | 7/10 |

From the above Table 18 results it has been concluded that:
Of the various levels of propylene glycol added to the composition, after repeated cycles of use the test subjects preferred the compositions incorporating propylene glycol at levels of 0.5%, 0.8% and 1.0%. Of these the level of 0.5% was somewhat preferred over the levels of 0.8% and 1.0%.

Consolidated Conclusions Relating to Emulsions Across all Tests D, E, F and Sites It is notable that for Tests D, E and F the preferred compositions chosen by the panellists at each of the sites were the same. This consistency of results is indicative of the experience of the panellists and clearly discernible differences in the results.

Test D

The majority of panellists across the three sites agreed on the composition with the preferred emollient with respect to skin feel. Their clear choice was the formulation with isopropyl myristate.

Test E

The majority of panellists agreed that the feel of the formula with IPM was significantly better than that of any other tested formulation. This was the case not only after the first application but more so after repeated applications. Similar results were obtained with the other formulations exemplified and at a range of isopropyl myristate concentrations up to 1.0% w/w and the most preferred level of isopropyl myristate was 0.5%.

In Tables 10 to 18 illustrate used Example 8, which contains triclosan as the biocide. Substitution of chlorhexidine gluconate for triclosan unsurprisingly gave substantially equivalent results with respect to skin feel.

As will be understood by those skilled in the art the antiseptic compositions can be formulated using other components and in other concentrations without departing from the inventive concept herein disclosed of incorporating isopropyl myristate to improve the feel of the product and enhance its propensity to be used.

Test F

As for Test D, the majority of panelists agreed on a composition with a preferred level of propylene glycol with respect to skin feel. The results were consistent across the cycles of use. The preferred composition incorporated propylene glycol at a level of 0.5%.

The invention claimed is:

1. An antiseptic hand rub composition which when used at a rate of less than 6 ml of composition for up to 60 seconds produces a level of bactericidal efficacy equal to or greater than that produced by 6 ml of 60% v/v aqueous isopropyl alcohol in 60 secs (as measured according to the test method of EN 1500:1997), said composition characterized in that it comprises:
ethanol 50-70% w/w,
dipropylene glycol 0.2-0.8% w/w;

phenoxyethanol 0.2-0.8% w/w; and
isopropyl myristate 0.1 to 0.3% w/w; and
free from any other myristic acid derivative.

2. The antiseptic hand rub composition according to claim 1 which produces substantially the same or better level of biocidal efficacy by hand rubbing for 30 seconds using 3 ml of the composition as is obtained using 6 ml of 60% v/v isopropyl alcohol in 60 seconds (as measured according to the test method of EN 1500:1997).

3. The antiseptic hand rub composition according to claim 1 free from isopropyl caproate, isopropyl laurate, isopropyl palmitate and isopropyl stearate.

4. The antiseptic hand rub composition according to claim 2 in the form of a gel.

5. The antiseptic hand rub composition according to claim 1 in the form of an emulsion or dispersion.

6. The antiseptic hand rub composition according to claim 5 free from isopropyl caproate, isopropyl laurate, isopropyl palmitate and isopropyl stearate.

7. The antiseptic hand rub composition of claim 1, wherein the composition exhibits no pilling after five applications to dry hands that are rubbed dry after each application and allowed five minutes between applications.

8. The antiseptic hand rub composition of claim 1, further comprising from 0.30% w/w to 0.40% w/w polyacrylic acid polymer.

* * * * *